United States Patent
Froestl

(10) Patent No.: US 7,498,319 B2
(45) Date of Patent: Mar. 3, 2009

(54) PHOSPHINIC ACID DERIVATIVES

(75) Inventor: Wolfgang Froestl, Ecublens (CH)

(73) Assignee: Novartis AG, Basel (CH)

( * ) Notice: Subject to any disclaimer, the term of this patent is extended or adjusted under 35 U.S.C. 154(b) by 172 days.

(21) Appl. No.: 10/576,972

(22) PCT Filed: Nov. 19, 2004

(86) PCT No.: PCT/EP2004/013177

§ 371 (c)(1),
(2), (4) Date: Apr. 25, 2006

(87) PCT Pub. No.: WO2005/054259

PCT Pub. Date: Jun. 16, 2005

(65) Prior Publication Data

US 2007/0259835 A1    Nov. 8, 2007

(30) Foreign Application Priority Data

Nov. 21, 2003    (GB) .................... 0327186.3

(51) Int. Cl.
*C07F 9/30* (2006.01)
*A61K 31/675* (2006.01)

(52) U.S. Cl. ............... 514/89; 546/22; 546/24
(58) Field of Classification Search ........... None
See application file for complete search history.

(56) References Cited

U.S. PATENT DOCUMENTS 5,332,729 A   7/1994   Mickel et al. ........... 514/114
5,376,684 A   12/1994  Mickel

FOREIGN PATENT DOCUMENTS

EP   0463560   1/1992
EP   0543780   5/1993

OTHER PUBLICATIONS

Zanger, M Gennaro, A. R., "Remington's Pharmaceutical Sciences", Remington's Pharmaceutical Sciences, Mack Publishing Co, US, 1975, pp. 454-469.

*Primary Examiner*—Zinna N Davis
(74) *Attorney, Agent, or Firm*—Foley & Lardner LLP

(57) ABSTRACT

The present invention relates to phosphinic acid derivatives as $GABA_B$ antagonists, their preparation, their use as pharmaceuticals and pharmaceutical compositions containing them.

17 Claims, No Drawings

PHOSPHINIC ACID DERIVATIVES

This application is a 371 of PCT/IN02/00235 filed Dec. 16, 2002 which claims priority to United Kingdom 0327186.3 filed Nov. 21, 2003.

The present invention relates to phosphinic acid derivatives as $GABA_B$ antagonists, their preparation, their use as pharmaceuticals and pharmaceutical compositions containing them.

More particularly, the invention provides a compound of formula I

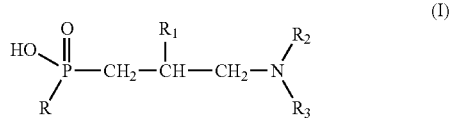

wherein

R is $(C_{3-5})$alkyl, di$(C_{1-4})$alkoxymethyl, $(C_{3-6})$cycloalkyl $(C_{1-4})$alkyl or benzyl optionally substituted in the aromatic ring by one to three radicals selected from $(C_{1-4})$alkyl, $(C_{1-4})$alkoxy and halo, $R_1$ is hydrogen or hydroxy, $R_2$ is a group of formula

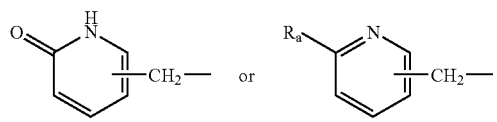

wherein $R_a$ is $(C_{1-4})$alkoxy, and $R_3$ is hydrogen or $(C_{1-4})$alkyl, or a salt thereof.

On account of their amphoteric nature, the compounds of formula I can form both acid addition salts and salts with bases.

Depending on the presence of asymmetric carbon atoms (e.g. when $R_1$ is hydroxy), the compounds of formula I and their salts may be in the form of isomeric mixtures, especially of racemates, or in the form of pure isomers, especially of optical antipodes.

Halo denotes fluorine, chlorine, bromine or iodine.

In a further aspect, the invention provides a process for the production of the compounds of formula I and their salts, which comprises, in a compound of formula II,

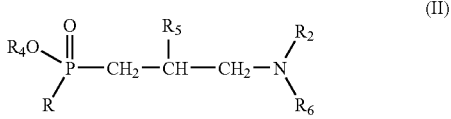

wherein R and $R_2$ are as defined above, $R_4$ is a hydroxy-protecting group, $R_5$ is hydrogen or protected hydroxy and $R_6$ is $R_3$ as defined above or an amino-protecting group, or in a salt thereof, freeing the hydroxy group by replacing the hydroxy-protecting group $R_4$ by hydrogen and, where appropriate, freeing the hydroxy group $R_1$ from the protected hydroxy group $R_5$, removing the amino-protecting group $R_6$ and, if desired, converting a resulting compound into a different compound of formula I, separating a mixture of isomers into its components and/or converting a salt into the corresponding free compound or vice-versa.

Suitable hydroxy-protecting and amino-protecting groups are well known from the literature. Also the steps of freeing the hydroxy groups and removing the amino-protecting groups can be effected in conventional manner.

The subsequent conversion steps can be carried out in succession or simultaneously in accordance with methods known per se.

Preferably, all the hydroxy- and amino-protecting groups are replaced by hydrogen in a single step by treatment with a tri-lower alkylsilyl halide, such as trimethylbromosilane, or with an acid, preferably a hydrohalic acid, e.g. hydrochloric acid, under hydrolytic conditions.

The starting materials of formula II can be prepared for example by reacting in customary manner a compound of formula III

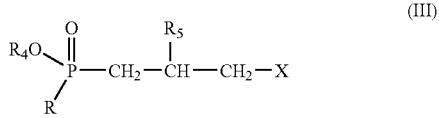

wherein R, $R_4$ and $R_5$ are as defined above and X is halogen, preferably chlorine, bromine or iodine, with a compound of formula IV

wherein $R_2$ and $R_6$ are as defined above.

The compounds of formula III and IV are known or may be produced in analogous manner to known procedures.

The novel compounds of formula I and their pharmaceutically acceptable salts, hereinafter referred to as the agents of the invention, have valuable $GABA_B$-antagonistic properties. In particular, they exhibit effective binding to the $GABA_B$-receptor and prove to be antagonists of GABA (γ-aminobutyric acid) at that receptor.

The agents of the invention interact at the $GABA_B$-receptor with $IC_{50}$ values of approximately $10^{-8}$M (moles/l) and above in cerebral cortex membranes of rats. In contrast to $GABA_B$-agonists such as baclofen, they do not potentiate the stimulation of adenylate cyclase by noradrenalin in sections of rat cerebral cortex, but act as an antagonist to the action of baclofen. The antagonism to baclofen can also be demonstrated in vitro in electrophysiological models, for example the penicillin-induced "epileptic" hippocampus section preparation, where baclofen in a concentration of 6 μM inhibits "epilepsy-like" discharges of pyramidal cells. The agents of the invention act as antagonists to baclofen at concentrations of from approximately 10 to approximately 100 μM. In vivo, the antagonism can be demonstrated by iontophoresis of baclofen in the cerebral cortex of rats and by systemic administration of antagonists in doses of from 10 to 100 mg/kg. At doses of approximately 30 mg/kg, antagonism to the muscle-relaxing action of baclofen occurs, which is measured in the Rotarod model.

The agents of the invention not only exhibit antagonism to baclofen, but also exhibit an independent action as antagonists to endogenous GABA. Accordingly, the antagonists are active in conventional behavioural models which are characteristic of anti-depressive, anxiolytic and/or nootropic properties. It has been found that compounds of formula I are active on oral administration in the floating test according to Porsolt, in the Geller test, the delayed passive avoidance test (single-attempt modification) in pre-test and post-test situations, in the two-chamber test and the complex labyrinth. Moreover, in studies on Rhesus monkeys an increased play instinct, curiosity, social grooming behaviour and a reduction in anxiety symptoms were observed.

The agents of the invention are therefore suitable as nootropics, anti-depressants and anxiolytics, and for the treatment of symptoms of cerebral insufficiency, cognition deficits, depression, esp. emotional depression, Alzheimer's disease, mild cognitive impairment, schizophrenia, or cognitive deficits, for example in patients suffering from Alzheimer's disease, mild cognitive impairment, or schizophrenia.

Moreover it has been found that the agents of the invention have pronounced anti-absence properties in vivo.

These properties can be demonstrated in a particular strain of rats on the basis of their pronounced inhibitory action on spontaneous "spike and wave" discharges in the animal model for absence epilepsy described in Vergnes et al. Neurosci. Lett. 33, 97-101 (1982). The agents of the invention are therefore suitable as active ingredients in anti-epileptic medicaments for the treatment of epilepsies of the "petit mal" type, both of spontaneous absence epilepsies, such as spontaneous absence epilepsies in children and young people, and atypical absences, such as absences of the Lennox-Gastaut syndrome, and also of absences that occur as undesired side effects in the case of treatment with conventional "grand mal" anti-epileptics, such as phenytoin, carbamazepine or Vigabatrin® and anti-epileptics having the same or a similar activity profile.

For the above-mentioned indications, the appropriate dosage will of course vary depending upon, for example, the compound employed, the host, the mode of administration and the nature and severity of the condition being treated. However, in general, satisfactory results in animals are indicated to be obtained at a daily dosage of from about 0.1 to about 100 mg/kg animal body weight. In larger mammals, for example humans, an indicated daily dosage is in the range from about 5 to about 500 mg of an agent of the invention, conveniently administered, for example, in divided doses up to four times a day or in sustained release form.

The agents of the invention may be administered by any conventional route, in particular enterally, preferably orally, for example in the form of tablets or capsules, or parenterally, for example in the form of injectable solutions or suspensions.

In accordance with the foregoing, the present invention also provides an agent of the invention, for use as a pharmaceutical, e.g. for the treatment of cerebral insufficiency, depression, anxiety and epilepsy.

The present invention furthermore provides a pharmaceutical composition comprising an agent of the invention in association with at least one pharmaceutical carrier or diluent. Such compositions may be manufactured in conventional manner. Unit dosage forms contain, for example, from about 0.25 to about 150, preferably from 0.25 to about 25 mg of a compound according to the invention.

Moreover the present invention provides the use of an agent of the invention, for the manufacture of a medicament for the treatment of any condition mentioned above, e.g. epilepsy, cerebral insufficiency, depression and anxiety.

In still a further aspect the present invention provides a method for the treatment of any condition mentioned above, e.g. epilepsy of the "petit mal" type, cerebral insufficiency, depression and anxiety, in a subject in need of such treatment, which comprises administering to such subject a therapeutically effective amount of an agent of the invention.

The following examples illustrate the invention.

EXAMPLE 1

{3-[(6-methoxy-3-pyridylmethyl)-amino]-2-(S)-hydroxy-propyl}-(cyclohexylmethyl)-]phosphinic acid A solution of 15.5 g (40.3 mmoles) of ethyl {3-[(6-methoxy-3-pyridylmethyl)-amino]-2-(S)-hydroxy-propyl}-(cyclohexylmethyl)-phosphinate in 1 liter of ethanol is treated with 806 mL of a 0.1 N aqueous sodium hydroxide solution and heated to reflux under stirring for 5 h. After cooling to room temperature the ethanol is evaporated in vacuo. After addition of 800 mL 0.1 N hydrochloric acid the aqueous solution is extracted once with 250 mL of dichloromethane and twice with 250 mL each of di-ethyl ether. The aqueous solution is evaporated to dryness in vacuo and dissolved in hot n-propanol. After filtration from sodium chloride the solution is again evaporated, the residue dissolved in methanol and treated with a solution of hydrochlorid acid gas in di-ethyl ether until a pH of one is reached. After evaporation of the solvent the resulting {3-[(6-methoxy-3-pyridylmethyl)-amino]-2-(S)-hydroxy-propyl}-(cyclohexylmethyl)-phosphinic acid monohydrochloride is recrystal-lized from isopropanol with dropwise addition of acetone. Mp 189-191° C.

7.9 (20 mmol) of the above hydrochloric acid salt are dissolved in 60 mL methanol and 300 mL of propyleneoxide are added slowly with vigorous stirring. The suspension is stirred at room temperature for 24 h and the product collected by filtration to give, after drying {3-[(6-methoxy-3-pyridylmethyl)-amino]-2-(S)-hydroxy-propyl}-(cyclohexylmethyl)-phosphinic acid of mp. 192-195° C.

$^1$HNMR (360 MHz, $D_2O$) δ 8.18 (d, J=2 Hz, 1H), 7.84 (dd, J=7 and 2 Hz, 1H), 6.93 (d, J=7 Hz, 1H), 4.31 (s, 2H), 4.30-4.13 (m, 1H), 3.89 (s, 3H), 3.25 and 3.4 (ABX, J=15 and 12 and 6 Hz, 2H), 1.90-1.67 (m, 4H, P—$CH_2$), 1.67-1.50 (m, 4H), 1.50-1.37 (m, 2H), 1.29-0.90 (m, 5H). $[\alpha]_D$=−9.8° (c=1.045 in MeOH), $[\alpha]_{365}$=−27.8° (c=1.045 in MeOH). Found C, 57.1; H, 8.3; N, 7.7; P, 8.7%. $C_{17}H_{29}N_2O_4P$ requires C, 57.29; H, 8.20; N, 7.86; P, 8.69%.

The starting material is prepared as follows:

A solution of 18.4 g (65 mmol) of ethyl (3-chloro-2-(R)-hydroxypropyl)(cyclohexylmethyl)phosphinate, prepared according to W. Froestl et al., J. Med. Chem. 38, 3313 (1995) in 90 mL dry ethanol under argon is treated with a solution of 9 g (65 mmol) of 6-methoxy-pyridyl-3-methaneamine prepared according to H. S. Forrest and J. Walter, J. Chem. Soc. 1948, 1939 in 90 mL of dry ethanol. After dropwise addition of 8.4 g (65 mmol) of ethyl diisopropylamine under stirring the solution is heated to reflux for 10 days, cooled to room temperature and the solvent evaporated. The oily residue is partitioned between dichloromethane and water, the organic layer separated, dried over sodium sulfate and filtered. The solvent is removed in vacuo to give a pale yellow oil. Chromatography on 1 kg of silica gel using initially dichloromethane, followed sequentially by dichloromethane/methanol 49:1, 19:1 and 9:1 mixtures gives ethyl {3-[(6-methoxy-3-pyridylmethyl)-amino]-2-(S)-hydroxy-propyl)} (cyclohexylmethyl)-phosphinate as an oily 1:1 mixture of diastereoisomers.

$^1$HNMR (500 MHz, $CDCl_3$) δ 8.05 (d, J=2 Hz, 2×1H), 7.54 (dd, J=7 and 2 Hz, 2×1H), 6.70 (d, J=7 Hz, 2×1H), 4.19-4.10

(m, 1H, one of CHOH diastereomer), 4.10-3.99 (m, 1H, one of CHOH diastereomer and 2×2H, ArCH$_2$N), 3.92 (s, 2×3H), 3.72 (q, J=7 Hz, 2×2H), 2.73-2.66 (m, 2×1H), 2.63-2.55 (m, 2×1H), 1.98-1.79 (m, 2×4H), 1.79-1.57 (m, 2×5H), 1.30 (t, J=7 Hz, 2×3H), 1.28-1.21 (m, 2×2H), 1.17-1.07 (m, 2×1H), 1.07-0.95 (m, 2×2H). MS m/e 385 (M+H)$^+$ for C$_{19}$H$_{34}$N$_2$O$_4$P (385.44).

The following compounds can be prepared in analogous manner to Example 1:

EXAMPLE 2

{3-[(2-methoxy-4-pyridylmethyl)-amino]-2-(S)-hydroxy-propyl}-(cyclohexylmethyl)-phosphinic acid Mp. 188-191° C. (recrystallized from methanol).
$^1$HNMR (360 MHz, D$_2$O) δ 8.15 (d, J=7 Hz, 1H), 7.08 (dd, J=7 and 1 Hz, 1H), 6.93 (d, J=1 Hz, 1H), 4.27-4.16 (m, 1H), 4.23 (s, 2H), 3.90 (s, 3H), 3.23 and 3.03 (ABX, J=15 and 12 and 6 Hz, 2H), 1.90-1.68 (m, 4H, P—CH$_2$), 1.65-1.50 (m, 4H), 1.48-1.38 (m, 2H), 1.28-0.90 (m, 5H). [α]$_D$=−9.2° (c=1.025 in MeOH), [α]$_{365}$=−25.8° (c=1.025 in MeOH). Found C, 57.4; H, 8.1; N, 8.1; P, 8.8%. C$_{17}$H$_{29}$N$_2$O$_4$P requires C, 57.29; H, 8.20; N, 7.86; P, 8.69%. The hydrochloride melts at 159-160° C. (recrystallized from isopropanol).

EXAMPLE 3

{3-[(6-methoxy-3-pyridylmethyl)-amino]-2-(S)-hydroxy-propyl}-(benzyl)-phosphinic acid Mp. 211-213° C. (recrystallized from methanol/diethyl-ether).
$^1$HNMR (360 MHz, D$_2$O) δ 8.12 (d, J=2 Hz, 1H), 7.84 (dd, J=7 and 2 Hz, 1H), 7.40-7.22 (m, 5H), 6.96 (d, J=7 Hz, 1H), 4.18 (s, 2H), 4.18-4.08 (m, 1H), 3.92 (s, 3H), 3.20 and 2.99 (ABX, J=15 and 12 and 6 Hz, 2H), 2.99 (d, J=18 Hz, 2H, P—CH$_2$Ph), 1.92-1.67 (m, 2H, P—CH$_2$). [α]$_D$=−10.1° (c=1.015 in MeOH); [α]$_{365}$=−29.6° (c=1.015 in MeOH); Found C, 56.9; H, 6.5; N, 7.7; P, 8.7; H$_2$O, 1.55%. C$_{17}$H$_{23}$N$_2$O$_4$P. 0.31H$_2$O requires C, 57.37; H, 6.69; N, 7.87; P, 8.70%, H$_2$O, 1.57%.

EXAMPLE 4

{3-[(2-methoxy-4-pyridylmethyl)-amino]-2-(S)-hydroxy-propyl}-(benzyl)phosphinic acid Mp. 192-195° C. (recrystallized from methanol/diethyl-ether).
$^1$HNMR (360 MHz, D$_2$O) δ 8.18 (d, J=7 Hz, 1H), 7.38-7.23 (m, 5H), 7.08 (dd, J=7 and 2 Hz, 1H), 6.94 (d, J=2 Hz, 1H), 4.23-4.10 (m, 1H), 4.21 (s, 2H), 3.93 (s, 3H), 3.21 and 3.06 (ABX, J=15 and 12 and 6 Hz, 2H), 3.02 (d, J=18 Hz, 2H, PCH$_2$Ph), 1.92-1.67 (m, 2H, P—CH$_2$). [α]$_D$=−8.5° (c=1.005 in MeOH); [α]$_{365}$=−26.4° (c=1.005 in MeOH). Found C, 58.4; H, 6.7; N, 7.8; P, 8.7%. C$_{17}$H$_{23}$N$_2$O$_4$P requires C, 58.28; H, 6.62; N, 8.00; P 8.84%.

EXAMPLE 5

{3-[6-methoxy-3-pyridylmethyl)-amino]-2-(S)-hydroxy-propyl}-(diethoxy-methyl)-phosphinic acid White Foam
$^1$HNMR (360 MHz, D$_2$O) δ 8.18 (d, J=2 Hz, 1H), 7.84 (dd, J=7 and 2 Hz, 1H), 6.93 (d, J=7 Hz, 1H), 4.46 (d, J=2 Hz, 1H), 4.33-4.20 (m, 1H), 4.21 (s, 2H), 3.90 (s, 3H), 3.85-3.73 (m, 2H), 3.73-3.61 (m, 2H), 3.29 and 3.03 (dAB, J=12 and 2 Hz, 2H), 1.98-1.72 (m, 2H), 1.17 (t, J=7 Hz, 3H), 1.16 (t, J=7 Hz, 3H). [α]$_D$=−10.3° (c=1.05 in MeOH); [α]$_{436}$=−18.8° (c=1.05 in MeOH). Found C, 46.1; H, 7.6; N, 7.0; P, 8.3; H$_2$O, 6.9%. C$_{15}$H$_{27}$N$_2$O$_6$P. 1.49H$_2$O requires C, 46.29; H, 7.76; N, 7.20; P, 7.96; H$_2$O, 6.90%.

EXAMPLE 6

{3-[2-methoxy-4-pyridylmethyl)-amino]-2-(S)-hydroxy-propyl}-(diethoxy-methyl)-phosphinic acid White Foam
$^1$HNMR (360 MHz, MeOD) δ 8.18 (d, J=7 Hz, 1H), 7.11 (dd, J=7 and 1 Hz, 1H), 6.97 (d, J=1 Hz, 1H), 4.38 (d, J=2 Hz, 1H), 4.38-4.26 (m, 1H), 4.26 (s, 2H), 3.92 (s, 3H), 3.88-3.76 (m, 2H), 3.76-3.63 (m, 2H), 3.32 and 3.08 (dAB, J=12 and 2 Hz, 2H), 2.02-1.73 (m, 2H), 1.20 (t, J=7 Hz, 3H), 1.19 (t, J=7 Hz, 3H). MS m/e 363 (M+H)$^+$ for C$_{15}$H$_{29}$N$_2$O$_6$P (363.36). [α]$_D$=−10.5° (c=0.96 in MeOH); [α]$_{436}$=−20.4° (c=0.96 in MeOH). Found C, 48.2; H, 7.5; N, 7.8; P, 8.4; H$_2$O, 3.88%. C$_{15}$H$_{27}$N$_2$O$_6$P. 0.81H$_2$O requires C, 47.79; H, 7.65; N, 7.43; P, 8.22; H$_2$O, 3.87%.

EXAMPLE 7

{2-(S)-hydroxy-3-[6-oxo-1,6-dihydro-pyridin-3-ylmethyl)-amino]-propyl}-(cyclohexylmethyl)-phosphinic acid A solution of 4.6 g (12.9 mmol) of the compound of Example 1 in 200 mL of 2 N hydrochloric acid is heated to reflux under stirring for 20 h. After cooling to room temperature the solution is extracted twice with 100 mL each of di-ethylether, once with 100 mL of dichloromethane and is evaporated to dryness in vacuo. After recrystallization from methanol with dropwise addition of di-ethyl ether and a second recrystallization from methanol {2-(S)-hydroxy-3-[(6-oxo-1,6-dihydro-pyridin-3-ylmethyl)-amino]-propyl}-(cyclohexylmethyl)-phosphinic acid hydrochloride is obtained, mp. 224-225° C.
$^1$HNMR (500 MHz, D$_2$O) δ 7.77 (dd, J=7 and 2 Hz, 1H), 7.72 (d, J=2 Hz, 1H), 6.68 (d, J=7 Hz, 1H), 4.33-4.25 (m, 1H), 4.16 (s, 2H), 3.27 and 3.08 (ABX, J=15 and 12 and 6 Hz, 2H), 2.06-1.97 (m, 1H, P—CH$_2$), 1.95-1.86 (m, 1H, P—CH$_2$), 1.81-1.73 (m, 2H), 1.73-1.54 (m, 6H), 1.30-1.18 (m, 2H), 1.18-1.1.7 (m, 1H), 1.07-0.96 (m, 2H). [α]$_D$=−10.6° (c=0.385 in MeOH), [α]$_{365}$=−29.1° (c=0.385 in MeOH). MS m/e 341.3 (M−H)$^+$ for C$_{16}$H$_{26}$N$_2$O$_4$P (341.37). Found C, 50.3; H, 7.5; Cl, 9.2; N, 7.6; P, 8.2; H$_2$O, 1.28%. C$_{16}$H$_{27}$N$_2$O$_4$P.HCl.0.27 H$_2$O requires C, 50.08; H, 7.50; Cl, 9.24; N, 7.30; P, 8.07; H$_2$O, 1.27%.

The following compounds can be prepared in analogous manner to Example 7:

EXAMPLE 8

{2-(S)-hydroxy-3-[(2-oxo-1,2-dihydro-pyridin-4-ylmethyl)amino]-propyl}-(cyclohexylmethyl)-phosphinic acid The hydrochloride melts at 212-215° C. (recrystallised from methanol).
$^1$HNMR (360 MHz, D$_2$O) δ 7.60 (d, J=7 Hz, 1H), 6.70 (d, J=2 Hz, 1H), 6.60 (dd, J=7 Hz and 2 Hz, 1H), 4.33-4.22 (m, 1H), 4.22 (s, 2H), 3.33 and 3.12 (ABX, J=15 and 12 and 6 Hz, 2H), 1.95-1.70 (m, 4H, P—CH$_2$), 1.70-1.53 (m, 4H), 1.53-

1.43 (m, 2H), 1.32-1.08 (m, 3H), 1.08-0.93 (m, 2H). $[\alpha]_D=-9.7°$ (c=0.205 in MeOH), $[\alpha]_{365}=-27.8°$ (c=0.205 in MeOH). Found C, 50.2; H, 7.6; Cl, 9.1; N, 7.4; P, 8.0; $H_2O$, 1.78%. $C_{16}H_{27}N_2O_4P.HCl.0.38\ H_2O$ requires C, 49.83; H, 7.52; Cl, 9.19; N 7.26; P 8.03; $H_2O$ 1.77%

EXAMPLE 9

{2-(S)-hydroxy-3-[(6-oxo-1,6-dihydro-pyridin-3-ylmethyl)-amino]-propyl}-(benzyl)-phosphinic acid The hydrochloride melts at 219-224° C. (recrystallised from methanol).

$^1$HNMR (360 MHz, $D_2O$) d 7.75 (dd, J=7 Hz and 2 Hz, 1H), 7.70 (d, J=2 Hz, 1H), 7.41-7.25 (m, 5H), 6.68 (d, J=7 Hz, 1H), 4.27-4.15 (m, 1H), 4.10 (s, 2H), 3.20 and 3.00 (ABX, J=15 and 12 and 6 Hz, 2H), 3.14 (d, J=18 Hz, 2H, $PCH_2Ph$), 2.05-1.81 (m, 2H, P—$CH_2$). $[\alpha]_D=-13.1°$ (c=0.275 in MeOH), $[\alpha]_{365}=-40.4°$ (c=0.275 in MeOH). Found C, 49.8; H, 6.2; Cl, 10.4; N, 7.4; P, 8.2; $H_2O$, 2.08%. $C_{16}H_{21}N_2O_4P.HCl.0.44H_2O$ requires C, 50.48; H, 6.06; Cl, 9.31; N, 7.36; P, 8.14; $H_2O$, 2.08%.

EXAMPLE 10

{2-(S)-hydroxy-3-[(2-oxo-1,2-dihydro-pyridin-4-ylmethyl)-amino]-propyl}-(benzyl)-phosphinic acid The hydrochloride melts at 226-228° C. (recrystallized from methanol/acetone/di-ethylether).

$^1$HNMR (360 MHz, $D_2O$) δ 7.61 (d, J=7 Hz, 1H), 7.42-7.27 (m, 5H), 6.68 (d, J=2 Hz, 1H), 6.58 (dd, J=7 Hz and 2 Hz, 1H), 4.32-4.20 (m, 1H), 4.18 (s, 2H), 3.25 and 3.08 (ABX, J=15 and 12 and 6 Hz, 2H), 3.16 (d, J=18 Hz, 2H, $PCH_2Ph$), 2.05-1.82 (m, 2H, P—$CH_2$). MS m/e 337 $(M+H)^+$ for $C_{16}H_{22}N_2O_4P$ (337.32). $[\alpha]_D=-13.6°$ (c=0.205 in MeOH), $[\alpha]_{365}=-36.6°$ (c=0.205 in MeOH). Found C, 51.1; H, 6.1; Cl, 9.4; N, 7.3; P, 8.3%. $C_{16}H_{21}N_2O_4P.HCl$ requires C, 51.55; H, 5.95; Cl, 9.51; N, 7.51; P, 8.31%.

The invention claimed is:

1. A compound of formula I

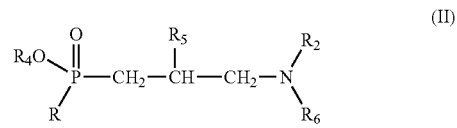

wherein:

R is $(C_{3-5})$alkyl, di$(C_{1-4})$alkoxymethyl, $(C_{3-6})$cycloalkyl $(C_{1-4})$alkyl or benzyl optionally substituted in the aromatic ring by one to three radicals selected from the group consisting of $(C_{1-4})$alkyl, $(C_{1-4})$alkoxy and halo, $R_1$ is hydrogen or hydroxy, $R_2$ is a group of formula

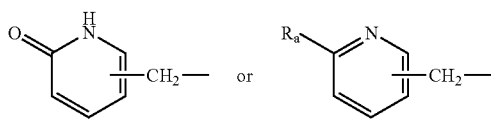

wherein $R_a$ is $(C_{1-4})$alkoxy, and $R_3$ is hydrogen or $(C_{1-4})$alkyl, or a salt thereof;

wherein the compound of formula I is selected from the group consisting of:

{3-[(6-methoxy-3-pyridylmethyl)-amino]-2-(S)-hydroxy-propyl}-(cyclohexylmethyl)-phosphinic acid;

{3-[(2-methoxy-4-pyridylmethyl)-amino]-2-(S)-hydroxy-propyl}-(cyclohexylmethyl)-phosphinic acid;

{3-[(6-methoxy-3-pyridylmethyl)-amino]-2-(S)-hydroxy-propyl}-(benzyl)-phosphinic acid;

{3-[(2-methoxy-4-pyridylmethyl)-amino]-2-(S)-hydroxy-propyl}-(benzyl)phosphinic acid;

{3-[6-methoxy-3-pyridylmethyl)-amino]-2-(S)-hydroxy-propyl}-(diethoxy-methyl)-phosphinic acid;

{3-[2-methoxy-4-pyridylmethyl)-amino]-2-(S)-hydroxy-propyl}-(diethoxy-methyl)-phosphinic acid;

{2-(S)-hydroxy-3-[6-oxo-1,6-dihydro-pyridin-3-ylmethyl)-amino]-propyl}-(cyclohexylmethyl)-phosphinic acid;

{2-(S)-hydroxy-3-[(2-oxo-1,2-dihydro-pyridin-4-ylmethyl)amino]-propyl}-(cyclohexylmethyl)-phosphinic acid;

{2-(S)-hydroxy-3-[(6-oxo-1,6-dihydro-pyridin-3-ylmethyl)-amino]-propyl}-(benzyl)-phosphinic acid; and {2-(S)-hydroxy-3-[(2-oxo-1,2-dihydro-pyridin-4-ylmethyl)-amino]-propyl}-(benzyl)-phosphinic acid.

2. The compound of claim 1, which is {2-(S)-hydroxy-3-[(6-oxo-1,6-dihydro-pyridin-3-ylmethyl)-amino]-propyl}-(cyclohexylmethyl)-phosphinic acid, or a salt thereof.

3. A process for the production of the compound of formula I as defined in claim 1, the process comprising, in a compound of formula II

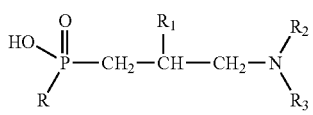

wherein R and $R_2$ are as defined in claim 1, $R_4$ is a hydroxy-protecting group, $R_5$ is hydrogen or protected hydroxyl, and $R_6$ is $R_3$ as defined in claim 1 or an amino-protecting group, or in a salt thereof, freeing the hydroxy group by replacing the hydroxy-protecting group $R_4$ by hydrogen and, where appropriate, freeing the hydroxy group $R_1$ from the protected hydroxy group $R_5$, and removing the amino-protecting group $R_6$.

4. The compound of claim 1, wherein the salt is a pharmaceutically acceptable salt.

5. A pharmaceutical composition comprising the compound of claim 4, in association with a pharmaceutical carrier or diluent.

6. A method for the treatment of epilepsy, cerebral insufficiency, cognition deficits, depression, schizophrenia, or anxiety in a subject in need of such treatment, the method comprising administering to the subject the compound of claim 1 or a pharmaceutically acceptable salt thereof.

7. A method for the treatment of epilepsy of the "petit mal" type, cerebral insufficiency, depression and anxiety, in a subject in need of such treatment, the method comprising administering to the subject a therapeutically effective amount of a compound of claim 1 or a pharmaceutically acceptable salt thereof.

8. The compound of claim 1, wherein the compound is {3-[(6-methoxy-3-pyridylmethyl)-amino]-2-(S)-hydroxy-propyl}-(cyclohexylmethyl)-phosphinic acid or a salt thereof.

9. The compound of claim 1, wherein the compound is {3-[(2-methoxy-4-pyridylmethyl)-amino]-2-(S)-hydroxy-propyl}-(cyclohexylmethyl)-phosphinic acid or a salt thereof.

10. The compound of claim 1, wherein the compound is {3-[(6-methoxy-3-pyridylmethyl)-amino]-2-(S)-hydroxy-propyl}-(benzyl)-phosphinic acid or a salt thereof.

11. The compound of claim 1, wherein the compound is {3-[(2-methoxy-4-pyridylmethyl)-amino]-2-(S)-hydroxy-propyl}-(benzyl)phosphinic acid or a salt thereof.

12. The compound of claim 1, wherein the compound is {3-[6-methoxy-3-pyridylmethyl)-amino]-2-(S)-hydroxy-propyl}-(diethoxy-methyl)-phosphinic acid or a salt thereof.

13. The compound of claim 1, wherein the compound is {3-[2-methoxy-4-pyridylmethyl)-amino]-2-(S)-hydroxy-propyl}-(diethoxy-methyl)-phosphinic acid or a salt thereof.

14. The compound of claim 1, wherein the compound is {2-(S)-hydroxy-3-[(2-oxo-1,2-dihydro-pyridin-4-ylmethyl)amino]-propyl}-(cyclohexylmethyl)-phosphinic acid or a salt thereof.

15. The compound of claim 1, wherein the compound is {2-(S)-hydroxy-3-[(6-oxo-1,6-dihydro-pyridin-3-ylmethyl)-amino]-propyl}-(benzyl)-phosphinic acid or a salt thereof.

16. The compound of claim 1, wherein the compound is {2-(S)-hydroxy-3-[(2-oxo-1,2-dihydro-pyridin-4-ylmethyl)-amino]-propyl}-(benzyl)-phosphinic acid or a salt thereof.

17. The process of claim 3, further comprising:

converting a resulting compound into a different compound of formula I, separating a mixture of isomers into its components, or converting a salt of the compound into its corresponding free compound or vice-versa.

* * * * *